(12) United States Patent
Oda et al.

(10) Patent No.: US 7,109,044 B1
(45) Date of Patent: Sep. 19, 2006

(54) METHOD OF DETECTION AND DISEASE STATE MANAGEMENT FOR RENAL DISEASES

(75) Inventors: Hiroshi Oda, Ibaraki (JP); Kosuke Seiki, Ibaraki (JP); Hiroshi Nakajima, Ibaraki (JP); Nobuyuki Sato, Ibaraki (JP); Yoshihiro Urade, Kyoto (JP); Nobuhito Hirawa, Kanagawa (JP); Yoshio Uehara, Tokyo (JP)

(73) Assignee: Maruha Corporation, Tokyo (JP)

( * ) Notice: Subject to any disclaimer, the term of this patent is extended or adjusted under 35 U.S.C. 154(b) by 0 days.

(21) Appl. No.: 09/786,503

(22) PCT Filed: Apr. 9, 1999

(86) PCT No.: PCT/JP99/04804

§ 371 (c)(1),
(2), (4) Date: Jun. 7, 2001

(87) PCT Pub. No.: WO00/14543

PCT Pub. Date: Mar. 16, 2000

(30) Foreign Application Priority Data

Sep. 4, 1998 (JP) ............................... 10-251450
May 13, 1999 (JP) ............................... 11-133050

(51) Int. Cl.
*G01N 33/53* (2006.01)
(52) U.S. Cl. .................... 436/811; 435/7.1; 435/7.92; 436/501
(58) Field of Classification Search ............... 435/7.1, 435/69.3, 7.4, 7.92–7.94; 436/811, 501
See application file for complete search history.

(56) References Cited

U.S. PATENT DOCUMENTS 6,122,540 A * 9/2000 Katzberg et al. ............ 600/419

FOREIGN PATENT DOCUMENTS

EP 0913405 5/1999

OTHER PUBLICATIONS

Andrea H., "Molecular Characterization of β-Trace Protein in Human Serum and Urine: A Potential Diagnostic Marker for Renal Diseases", Glycobiology, vol. 7, No. 4, p. 499-506 (1997).
Priem Friedrich et al., "beta-Trace protein in serum: A new marker of glomerular filtration rate in the creatinine-blind range", *Clinical Chemistry*, vol. 45, No. 4, pp. 567-568 XP-001080031, Apr. (1999).
Chemke J et al., "Pre Natal Diagnosis of Meckel Syndrome Alpha Feto Protein and Beta Trace Protein in Amniotic Fluid", *Clinical Genetics*, vol. 11, No. 4, pp. 285-289, XP-002202028, (1977).

* cited by examiner

*Primary Examiner*—Long V. Le
*Assistant Examiner*—Gary W. Counts
(74) *Attorney, Agent, or Firm*—Fish & Richardson P.C.

(57) ABSTRACT

The present invention relates to a method of detection of an early-stage renal disease, comprising determining the concentration of human lipocalin-type prostaglandin D synthase in a body fluid sample taken from a subject and comparing the determined concentration with a reference value set by determining the concentrations of human lipocalin-type prostaglandin D synthase in body fluid samples taken from healthy subjects; and a method of disease state management for a renal disease, comprising determining the concentration of human lipocalin-type prostaglandin D synthase in a body fluid sample taken from a subject and evaluating the glomerular filtration ability of the subject from the determined concentration.

2 Claims, 9 Drawing Sheets

METHOD OF DETECTION AND DISEASE STATE MANAGEMENT FOR RENAL DISEASES

TECHNICAL FIELD

The present invention relates to a method for detecting renal diseases. More specifically, the invention relates to a method for detecting early-stage renal diseases which are undetectable by existing diagnosis methods; and a method for managing the disease state of renal diseases by evaluating the glomerular filtration ability of patients in a simple manner.

BACKGROUND ART

Recently, the number of patients who begin to undergo dialysis therapy because of diabetic nephropathy is increasing year by year. According to statistical data in 1994, the number of patients with diabetic nephropathy who have newly started dialysis therapy in one year was 9,351, which is very close to the corresponding number 10,995 in patients with chronic glomerulonephritis (Akira Sekikawa et al., The 41$^{st}$ Annual Meeting of Japan Diabetes Society) Unfortunately, however, dialysis therapy for diabetic patients causes many problems such as cardiac failure, raising or lowering of blood pressure, infections or shunt troubles, and the average duration of life after the introduction of dialysis is as short as about 3 years (see, for example, Statistical Survey Committee of the Japanese Society for Dialysis Therapy, Journal of the Japanese Society for Dialysis Therapy, 25, 1095–1103, 1992). Thus, it is believed that early treatment by early diagnosis is important for diabetic nephropathy.

In diagnosis and disease state management for renal diseases such as diabetic nephropathy and glomerulonephritis that cause glomerular lesions, clearance tests using inulin, creatinine, etc. are considered bo be useful for the evaluation of glomerular filtration ability. However, clearance tests require timed urine. Also, in clearance tests where an exogenous substance such as inulin is administered, intravenous injection of the exogenous substance is required. Therefore, due to the time and labor required for such tests, application of a clearance test has been limited to patients with apparent renal diseases. Accordingly, it is rather rare to use a clearance test as a routine diagnosis method for those patients who are suspected of renal diseases or who may possibly have renal diseases. In many cases, diseases of such patients have been diagnosed by detecting persistent proteinuria or determining serum creatinine concentrations. However, it is also known that irreversible glomerular lesions have already progressed when persistent proteinuria appears or when serum creatinine concentrations increase (see, for example, "Nephrology", Kiyoshi Kurokawa (ed.), 249–251, 1995). Therefore, the detection of persistent proteinuria or the determination of serum creatinine concentration cannot be effective means to detect early-stage lesions.

Recently, it has become possible to determine various proteins excreted into urine. For example, it has become clear that albumin excretion in urine increases in diabetic nephropathy, i.e. microalbuminuria precedes persistent proteinuria. At present, it is a general practice to diagnose renal diseases with the appearance of microalbuminuria or the like.

Generally, diabetic nephropathy and other nephropathy are classified into the 1st stage (pre-nephropathy stage), the 2nd stage (early nephropathy stage), the 3rd stage (apparent nephropathy stage), the 4th stage (renal failure stage) and the 5th stage (dialysis therapy stage) (Yukio Shigeta et al., "1991 Diabetes Survey Report", Ministry of Health and Welfare, 317–320, 1992). The stage at which microalbuminuria is detected falls under the above-described 2nd stage (early nephropathy stage). Pathologically, mild to medium grade diffuse lesions are already present at this stage; the presence of nodular lesions is also known at this stage. For example, diabetic nephropathy is characterized by thickening of the glomerular basement membrane and expansion of the mesangial region. However, it is known that these changes are already present even at a stage when no microalbuminuria appeares clinically (Shigeki Inomata et al., Journal of the Japan Diabetes Society, 30, 429–435, 1987; Bangstad, H., J. et al., Diabetologia, 36, 523–529, 1993). Therefore, the 2nd stage (early nephropathy stage) does not necessarily mean the beginning of nephropathy, and is understood as the stage at which nephropathy becomes diagnosable by current clinical tests. On the other hand, it is believed that those abnormalities occurring at the 1st stage (pre-nephropathy stage) prior to the appearance of microalbuminuria can only be detected by renal biopsy. However, since renal biopsy is invasive, it involves pain and danger. Besides, it requires enormous labor and time from the beginning of biopsy to the obtainment of results. Therefore, the development of a simple, non-invasive test method is desired which can detect those abnormalities occurring prior to the appearance of microalbuminuria.

Under such circumstances, it was reported that urinary type-IV collagen excretion increases even at the pre-nephropathy stage, and the possibility that urinary type-IV collagen could be an earlier indicator of diabetic nephropathy has been suggested (Hayashi, Y. et al., Diabetic Medicine, 9, 366–370, 1992; Yagame, M. et al., J. Clin. Lab. Anal., 11, 110–116, 1997). It is believed that such increase of urinary type-IV collagen excretion reflects histological changes such as thickening of the glomerular basement membrane and mesangial expansion, and that the increase is the result of enhanced production of type-IV collagen in the glomerular basement membrane, glomerular epithelial cells or tubular epithelial cells (Motohide Isono et al., Journal of the Japan Diabetes Society, 39, 599–604, 1996). However, it is considered that even before the above-mentioned histological changes take place in the glomerulus, various changes in metabolism, morphology, etc. are occurring at the cell level, corresponding to hyperglycemia characteristic in diabetes. For example, up-regulation of protein kinase C activity has been reported in the glomeruli of diabetic rats, and glomerular or mesangial cells cultured under high glucose concentrations. The relation between this rise and histological changes in diabetic complications such as diabetic nephropathy is attracting attention (Craven, P., A. and DeRubertis, F. R., J. Clin. Invest., 83, 1667–1675, 1989; Williams, B. and Schrier, R. W., Diabetes, 41, 1464–1472, 1992). Therefore, if it is possible to detect these qualitative changes at the cellular level earlier, more effective treatment could be given before histological changes have occurred. However, no reports have been made to date which clinically examine such utility.

On the other hand, human lipocalin-type prostaglandin D synthase (hereinafter, referred to as "L-PGDS") is an enzyme which catalyzes the isomerization of $PGH_2$ (a common precursor of various prostaglandins) to $PGD_2$ that exhibits various physiological actions such as sleep induction (Urade, Y., Fujimoto, N. and Hayaishi, O., J. Biol. Chem., 260, 12410–12415, 1985; Urade, Y., Watanabe, K. and Hayaishi, O., J. Lipid Mediator Cell Signaling, 12, 257–273, 1995). Recently, it was revealed that this L-PGDS is identical with β-trace which was known to be present in human cerebrospinal fluid (CSF) abundantly (Hoffmann, A., Conradt, H. S., Gross, G., Nimitz, M., Lottspeich, F., and Wurster, U., J. Neurochem., 61, 451–456, 1993; Zahn, M. Mader, M., Schmidt, B., Bollensen, E. and Felgenhauer, K., Neurosci. Let., 154, 93–95, 1993; Watanabe, K., Urade, Y., Mader, M., Murphy, C. and Hayaishi, O., Biochem. Biophys. Res. Commun., 203, 1110–1116, 1994).

In 1969 when L-PGDS was still called β-trace, Ericsson et al. published a paper suggesting correlation between renal diseases and β-trace (L-PGDS) (Ericsson, J., Link, H. and Zettervall, O., Neurology, 19, 606–610, 1969). Since assay methods at that time were technically immature, L-PGDS was undetectable in serum and urine from healthy subjects, but it was detected in serum and urine from patients with renal diseases such as chronic glomerulonephritis in which abnormalities are recognized in serum creatinine concentration and creatinine clearance. It was suggested that L-PGDS concentrations increase in those patients. Felgenhauer et al. also reported that serum L-PGDS, which was not detected in healthy subjects, was detected though in only one patient with renal failure (Felgenhauer, K., Schadlich, H. J. and Nekic, M., Klin. Wochenschr., 65, 764–768, 1987). Against these findings, Whitsed et al. developed a more sensitive assay system, compared urinary L-PGDS concentrations (amounts excreted/24 hr) from healthy subjects and those from patients with renal diseases presenting proteinuria, and reported that patients with renal diseases not necessarily exhibited higher L-PGDS concentrations (Whitsed, H., and Penny, R., Clin. Chim. Acta, 50, 111–118, 1974). It is believed that the reason why researchers have such opposite opinions on the correlation between renal diseases and L-PGDS is because the assay system used in these reports are semi-quantitative methods based on classical immunological methods using polyclonal antibodies. Recently, using more quantitative assay system, Hoffmann et al. have confirmed that serum L-PGDS concentrations in patients with end-stage renal failure (at dialysis therapy stage) are remarkably increased as compared to the concentrations in healthy subjects (Hoffmann, A., Nimtz, M. and Conradt, H. S., Glycobiology, 7, 499–506, 1997). However, although they use monoclonal antibodies with clarified specificity, their assay method is complicated. Briefly, they purify L-PGDS from serum samples, and then compare the strength of the bands on Western blot. Thus, it is considered to be still difficult to accurately compare minor differences in concentration by this method.

As described above, any of the examinations concerning the correlation between renal diseases and L-PGDS made to date has merely detected a remarkable rise of L-PGDS concentrations in those patients who have been confirmed to have an evidently advanced renal disease by existing diagnostic methods, e.g. showing abnormality in creatinine kinetics, presenting proteinurea or being at dialysis therapy stage. On the contrary, no examinations have been made to date concerning L-PGDS concentrations prior to the progress of renal diseases.

DISCLOSURE OF THE INVENTION

It is an object of the invention to provide a method which can detect those renal abnormalities occurring prior to early-stage nephropathy that were undetectable by various diagnostic methods so far employed, accurately and without imposing a big burden on subjects. Further, it is another object of the invention to provide a method which can evaluate simply and in a short time glomerular filtration ability that has been evaluated so far by clearance tests requiring much time and labor.

The inventors have made intensive and extensive researches toward the solution of the above-mentioned problems. As a result, the inventors have found that it is possible to detect renal diseases prior to the early nephropathy stage at which diseases have progressed to some extent by determining L-PGDS concentrations in body fluid samples (e.g., serum, urine) and using the determined values as an indicator, and that it is also possible to manage the disease state of renal disease patients by using the determined values as an indicator. Thus, the present invention has been achieved.

The present invention relates to a method of early detection of a renal disease, comprising determining the concentration of L-PGDS in a body fluid sample taken from a subject and comparing the determined concentration with a reference value set by determining the concentrations of L-PGDS in body fluid samples taken from healthy subjects.

The present invention also related to a method of disease state management for a renal disease, comprising determining the concentration of L-PGDS in a body fluid sample taken from a subject and evaluating the glomerular filtration ability of the subject from the determined concentration.

Hereinbelow, the present invention will be described in detail.

In the present invention, samples to be used for L-PGDS assay are body fluid samples taken from subjects. Specifically, blood (serum or plasma), urine (spotted urine, timed urine, etc.), amniotic fluid, or the like may be used.

As a method for determining L-PGDS concentrations in the above-mentioned samples, any assay method may be used as long as it can determine L-PGDS concentrations accurately. For example, an immunological assay method or an enzyme activity assay method may be used. However, from the viewpoint of necessity to handle a large number of samples at one time and in a simple manner at actual clinical sites, it is preferable to employ an immunological assay method such as EIA, ELISA, RIA or FIA using L-PGDS specific monoclonal antibodies or polyclonal antibodies.

Of the above-described immunological assay methods, sandwich ELISA using L-PGDS specific monoclonal antibodies is especially preferable. Specific examples of the monoclonal antibodies include those antibodies produced by hybridoma cell strains 1B7 (FERM BP-5709), 7F5 (FERM BP-5711), 6F5 (FERM BP-5710), 9A6 (FERM BP-5712) and 10A3 (FERM BP-5713).

In the determination of L-PGDS concetration by sandwich ELISA, a L-PGDS detection kit established by the present inventors containing the above-described monoclonal antibodies may be used (WO 97/16461).

In the present invention, it is possible to detect an early-stage renal disease in a subject by using as an indicator the L-PGDS concentration determined by the above-mentioned means. Also, it is possible to manage the disease state of a subject's renal disease by evaluating the glomerular filtration ability of the subject using as an indicator the L-PGDS concentration determined by the above-mentioned means.

In the method of the invention, a renal disease is detected by comparing the L-PGDS concentration in a body fluid sample of a subject determined by the above-mentioned means with a reference value set by determining L-PGDS concentrations in body fluid samples of healthy subjects by the same means.

The term "reference value" used herein means the value to judge positive or negative. This value is also called the "cut-off value" at clinical site. This reference value may be set, for example, by the following formula:

Mean value in healthy subjects+(α×standard deviation) wherein α may be 0.5, 1, 2, 5 or the like. 2 is often used for α In populations which show regular distribution.

Specifically, the detection of a renal disease is performed as follows. First, L-PGDS concentrations in body fluid samples are determined on a population composed of healthy subjects to set a reference value by the above-described formula. Subsequently, if the L-PGDS concentration in a subject body fluid sample is above the reference value (i.e. shows abnormal value), the subject is judged positive.

Disease state management for a renal disease is performed by evaluating the glomerular filtration ability of a subject using the L-PGDS concentration in a body fluid sample of the subject determined by the above-mentioned means.

In the present invention, the term "disease state management" means to grasp the condition of a disease (the degree of severity) and to predict the behavior of the disease (prognosis).

As renal diseases which can be detected by the method of the invention or renal diseases of which the disease state can be managed by the method of the invention, renal diseases accompanied with glomerular lesions, renal diseases associated with hypertension, renal diseases associated with lipid metabolic disorder or the like may be enumerated. Specific examples include nephropathy, etc. More specifically, glomerulonephritis, nephrotic syndrome, diabetic nephropathy, polycystic kidney, renal failure or the like may be enumerated. The term "diabetic nephropathy" used herein include diabetic nephropathy of extremely early stage, for example, before microalbuminuria appears or before urinary type-IV collagen increases.

BEST MODES FOR CARRYING OUT THE INVENTION

Figure 1:
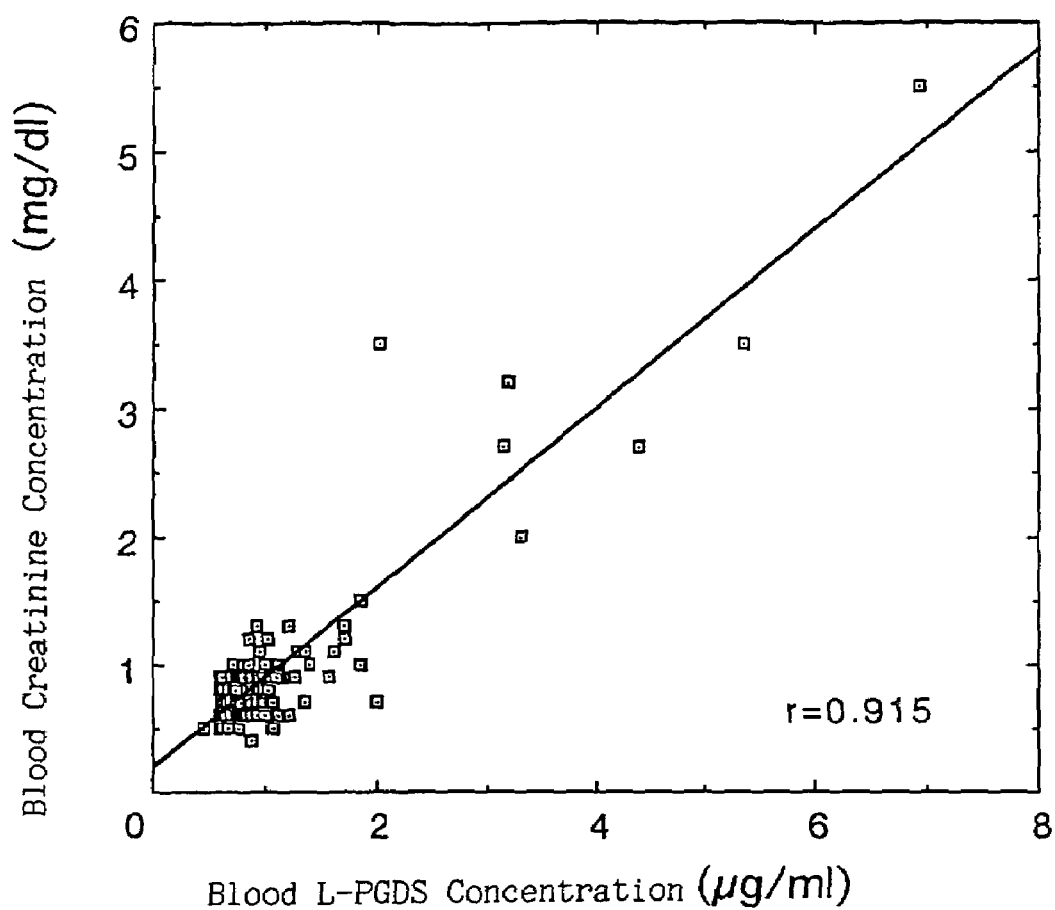
FIG. 1 shows correlation between serum L-PGDS concentration and serum creatinine concentration.

Hereinbelow, the present invention will be described in more detail with reference to the following Examples, which should not be construed as limiting the scope of the invention.

REFERENCE EXAMPLE 1

Determination of Serum and Urinary L-PGDS Concentrations in Healthy Persons and the Setting of Reference Values Using blood (serum) samples and spotted urine samples taken from healthy subjects, L-PGDS concentrations in these body fluid samples were determined by sandwich ELISA to set reference values.

(1) Preparation of A Standard Curve

First, an anti-L-PGDS monoclonal antibody (clone: 7F5) which can bind to L-PGDS was diluted with 50 mM carbonate buffer (pH 9.6) to give a concentration of 4.4 µg/ml. Then, this diluted antibody was added to a 96-well microtiter plate at 300 µl/well and left overnight at 4° C. to thereby immobilize the antibody on the plate. This plate was washed with phosphate buffered saline (pH 7.4; hereinafter called "PBS") three times. Thereafter, 0.2% casein-containing PBS (pH 7.4; hereinafter called the "blocking solution") was added to the plate at 300 µl/well and incubated at 30° C. for 90 min for blocking.

Subsequently, the plate after blocking was washed with 0.05% Tween 20-containing PBS (T-PBS) three times. Then, 100 µl of reference L-PGDS solution (which was prepared by stepwise dilution of L-PGDS purified from CSF with the blocking solution) was added to each well and incubated at 30° C. for 90 min. After the reaction, the plate was washed with T-PBS three times. Then, 100 µl of horseradish peroxidase-labelled anti-L-PGDS monoclonal antibody (clone: 1B7) diluted with the blocking solution to give a concentration of 0.5 µg/ml was incubated at 30° C. for 90 min. After the plate was washed with T-PBS three times, 100 µl of a chromogenic substrate solution (ABTS solution; Boehringer Mannheim) was added to each well and incubated at 30° C. for 30 min. Then, 100 µl of a stopping solution (1.5% oxalic acid) was added to each well and agitated with a plate mixer to terminate the reaction. Using a commercial plate reader (model SK601; manufactured by Seikagaku Corp.), the difference between the absorbances at 405 nm and 490 nm (A405 nm–A490 nm) was determined to thereby prepare a reference curve.

The monoclonal antibodies (clones: 1B7 and 7F5) used in the above sandwich ELISA were obtained as follows. Briefly, 1.0 ml of pristan was injected into mice intraperitoneally. Two weeks later, each antibody-producing hybridoma cell strain was transplanted into the peritoneal cavity of the mice ($1\times10^8$ cells/mouse). Two weeks thereafter, ascites fluid was collected from each mouse and subjected to protein A affinity column chromatography to obtain the monoclonal antibody of interest (3–10 mg/ml).

The designations of the above-mentioned monoclonal antibody-producing hybridoma cell strains coincide with the designations of the above-mentioned monoclonal antibodies. These cell strains, 1B7 and 7F5, were deposited at the National Institute of Bioscience and Human-Technology, Agency of Industrial Science and Technology (1–3, Higashi 1-chome, Tsukuba City Ibaraki Pref., Japan) under the Accession Numbers of FERM BP-5709 (original deposit date: Sep. 21, 1995) and FERM BP-5711 (original deposit date: Jun. 6, 1996), respectively.

(2) Determination of L-PGDS Concentrations in Samples

One hundred and ninety-two serum samples and 56 spotted urine samples were used. After these samples were appropriately diluted with the blocking solution, L-PGDS concentrations were determined by the sandwich ELISA as described above. The results of the assay revealed that the mean value±standard deviation of serum L-PGDS concentration obtained from healthy subjects was 0.848±0.186 µg/ml. In the analysis using spotted urine samples, the determined values were converted into urinary L-PGDS indexes (L-PGDS/g creatinine) using urinary creatinine concentrations, considering influences of the difference in urinary concentrations depending on the time of sampling. As a result, the mean value±standard deviation of urinary L-PGDS index obtained from healthy subjects was 2.44±1.86 mg/g creatinine. From the thus obtained mean value±standard deviation, a reference value was set according to the formula described earlier, i.e. the mean value+ ($2\times$standard deviation). The reference value for serum L-PGDS concentration was 1.22 µg/ml and the reference value for urinary L-PGDS index was 6.16 mg/g creatinine.

In the following Examples, L-PGDS in body fluid samples (i.e. serum and urine) was determined in the same manner as described in the Reference Example; creatinine in those samples was determined by the alkaline picrate method; urinary albumin was determined by the latex agglutination method; and urinary type-IV collagen was measured by the sandwich ELISA. Since spotted urine was used as urine samples, determined values from these samples were converted into values per gram of creatinine in urine taking the difference in urinary concentrations into consideration (urinary L-PGDS index: L-PGDS/g creatinine; urinary albumin index: albumin/g creatinine; urinary type-IV collagen index: type-IV collagen/g creatinine).

EXAMPLE 1

Correlation Between L-PGDS and Serum Creatinine/Urinary Albumin/Urinary Collagen IV Serum L-PGDS concentration, serum creatinine concentration, urinary L-PGDS index and urinary albumin index were determined on 118 internal medicine outpatients. Also, urinary L-PGDS index and urinary type-IV collagen index were determined on 284 internal medicine outpatients.

Figure 2:
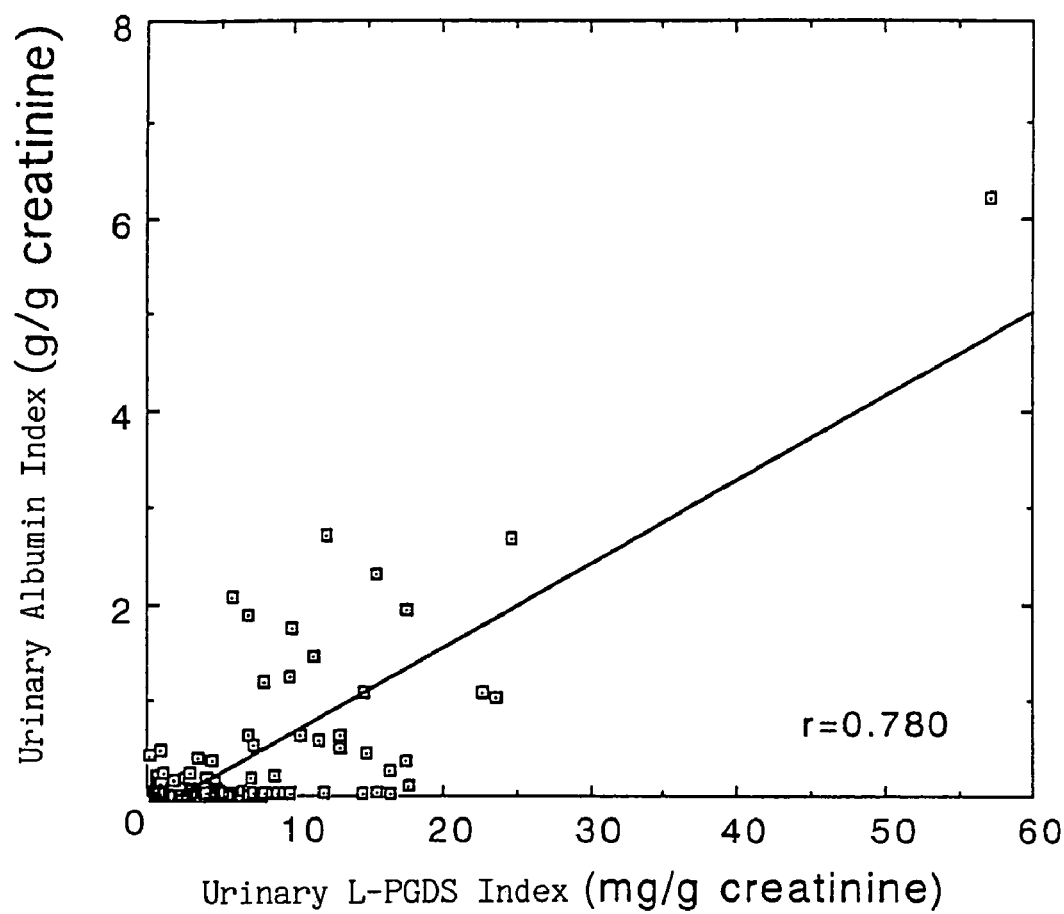
FIG. 2 shows correlation between urinary L-PGDS index and urinary albumin index.
Figure 3:
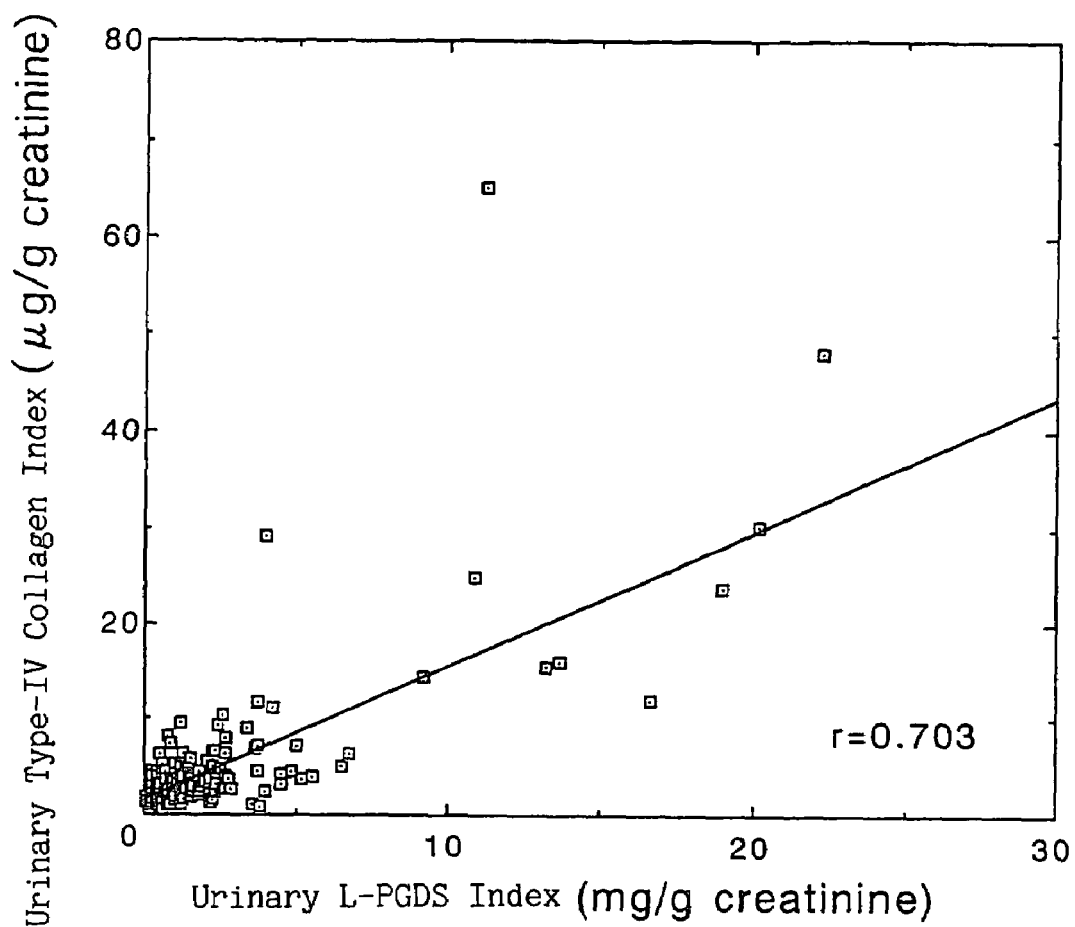
FIG. 3 shows correlation between urinary L-PGDS index and urinary type-IV collagen index.

As shown discretely in FIGS. 1 to 3, a high correlation was found between serum L-PGDS concentration and serum creatinine concentration, between urinary L-PGDS index and urinary albumin index and between urinary L-PGDS index and urinary type-IV collagen index. Therefore, it has become evident that L-PGDS can be an indicator of renal diseases which is comparable to serum creatinine, urinary albumin and urinary type-IV collagen used so far.

EXAMPLE 2

Changes in L-PGDS Concentrations in Patients with Various Renal Diseases

Serum L-PGDS concentration and urinary L-PGDS index were determined on 42 patients with renal diseases (chronic renal failure: 11 patients; glomerulonephritis: 23 patients; polycystic kidney: 8 patients). At the same time, serum creatinine concentration and urinary albumin index were determined. The results are shown in FIG. 4.

Figure 4:
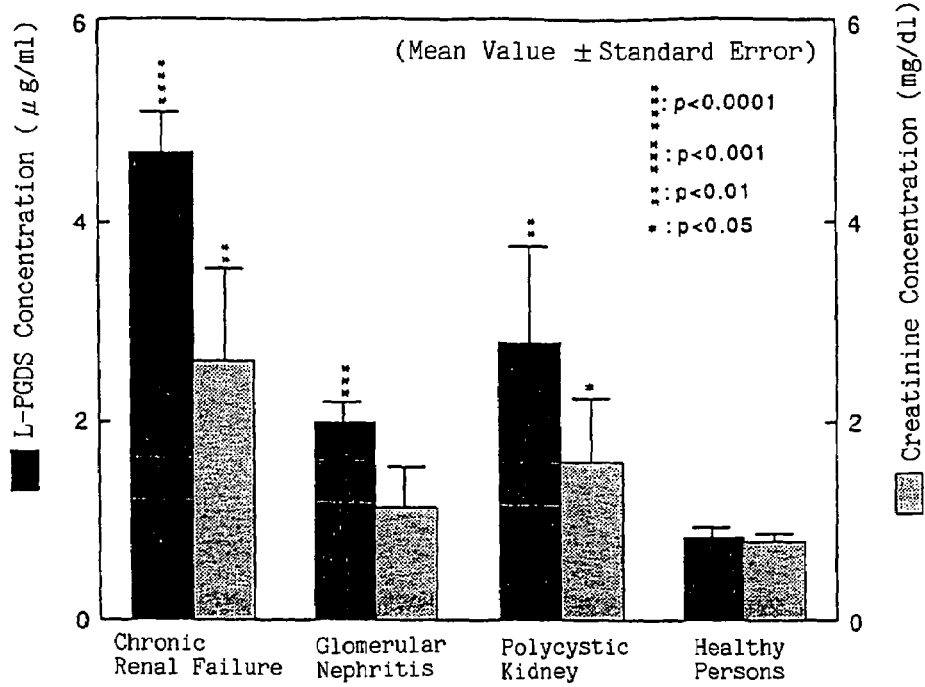
FIG. 4 shows serum L-PGDS concentration and serum creatinine concentration (Panel A) and urinary L-PGDS index and urinary albumin index (Panel B) in patients with various renal diseases.
Figure 4:
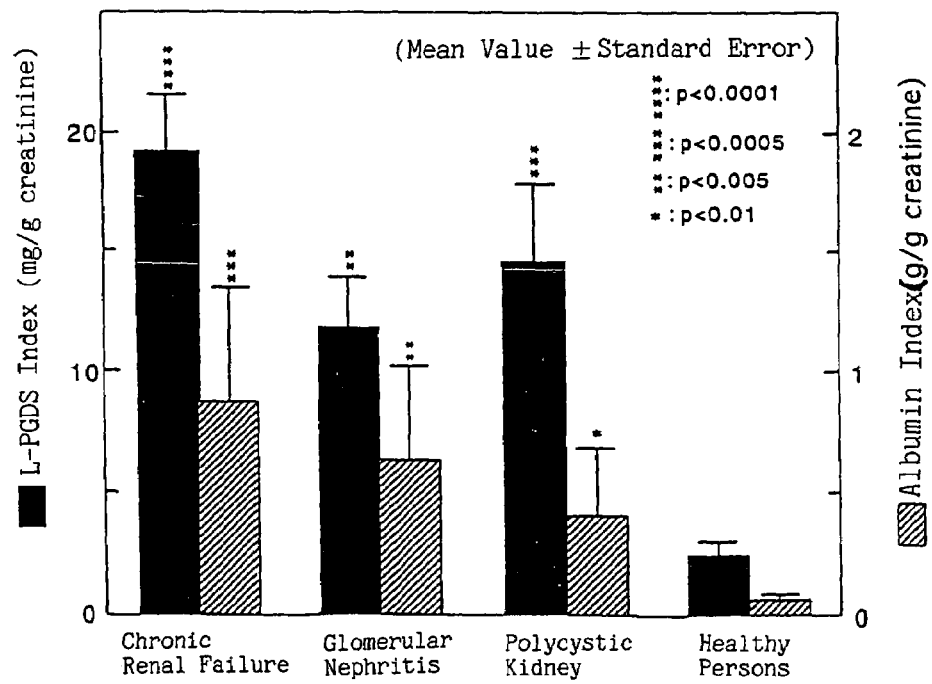

As shown in FIG. 4, it has become clear that in all of the renal diseases tested, serum L-PGDS concentration and urinary L-PGDS index increase significantly compared to those values in healthy subjects. Serum creatinine concentration and urinary albumin index also increased in those renal diseases. However, comparing the p values (levels of significance), L-PGDS showed smaller p values. Therefore, we can say that L-PGDS can be an indicator of renal diseases superior to serum creatinine and urinary albumin.

EXAMPLE 3

Changes in L-PGDS Concentrations in Diabetic Patients

Serum L-PGDS concentration and uninary L-PGDS index were determined on 55 diabetic patients. At the same time, serum creatinine concentration and urinary albumin index were determined. The patients were classified according to the history of their diabetes (less than 5 years: 22; from 5 years to less than 10 years: 19; 10 years or more: 14). The results are shown in FIG. 5.

Figure 5:
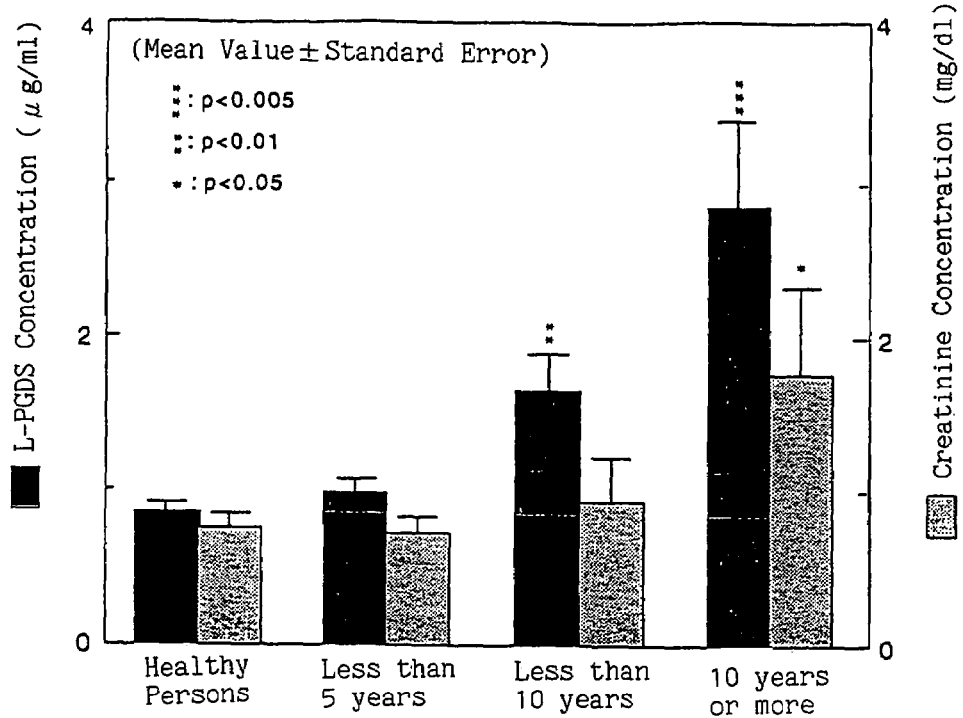
FIG. 5 shows correlation between serum L-PGDS concentration/serum creatinine concentration and the history of diabetes (Panel A) and correlation between urinary L-PGDS index/urinary albumin index and the history of diabetes (Panel B).
Figure 5:
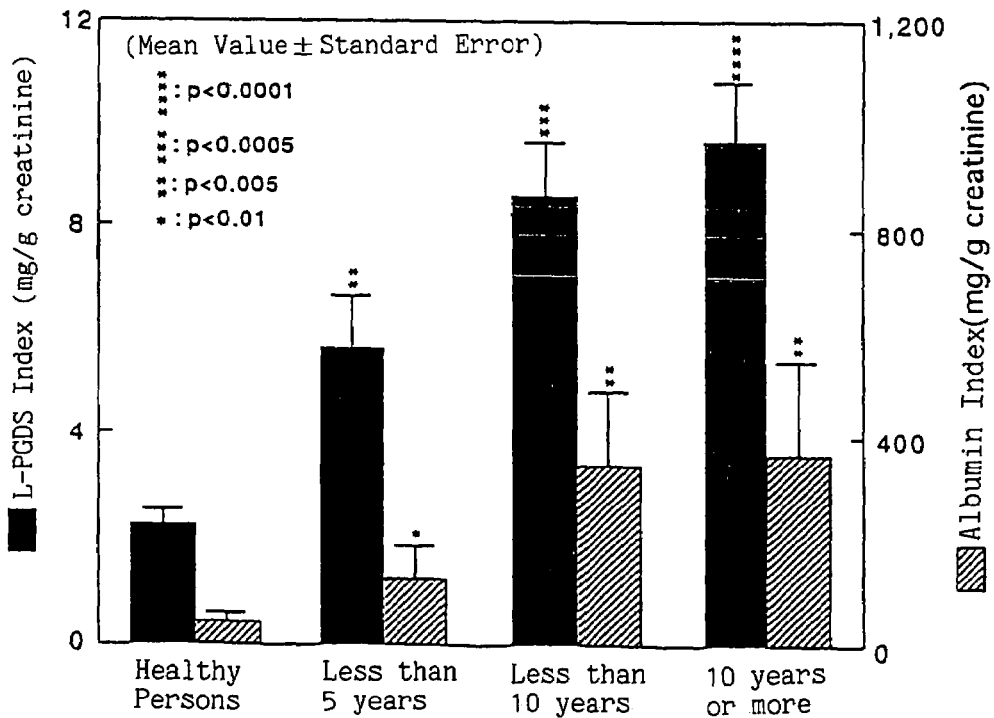

As shown in FIG. 5, it was found that the longer the disease history is, the more both serum L-PGDS concentration and uninary L-PGDS index increase. Serum creatinine concentration and urinary albumin index also increased as the disease history was longer. However, comparing the p values (levels of significance), L-PGDS showed smaller p values. Since diabetes easily becomes complicated by nephropathy, we can say that L-PGDS can be an indicator of progression of diabetic nephropathy superior to serum creatinine and urinary albumin.

EXAMPLE 4

Prospective Study of Diabetic Patients

A two-year prospective study was performed on the 6 patients who were normal in both serum creatinine concentration and urinary albumin index but abnormal in serum L-PGDS concentration and/or urinary L-PGDS index in Example 3. In this study, abnormal values were defined as follows. As to L-PGDS, the mean value +($2\times$standard deviation) obtained from healthy subjects (i.e., 1.22 µg/ml for serum L-PGDS concentration and 6.16 mg/g creatinine for urinary L-PGDS index) or more was considered abnormal. As to serum creatinine concentration, 1.1 mg/dl or more was considered abnormal. As to urinary albumin index, 30 mg/g creatinine or more was considered abnormal. The results are shown in Table 1.

TABLE 1

Follow-up Survey on Diabetic Patients

|  | Subject 1 | Subject 2 | Subject 3 | Subject 4 | Subject 5 | Subject 6 |
|---|---|---|---|---|---|---|
| [At the beginning of the test] | | | | | | |
| Blood creatinine concentration (mg/dl) | 0.9 | 1.0 | 0.8 | 0.7 | 0.9 | 0.7 |
| Urinary albumin index (mg/g creatinine) | 15.9 | 28.8 | 15.2 | 19.4 | 8.8 | 10.1 |
| Blood L-PGDS concentration (μg/ml) | 1.86* | 1.69* | 1.25* | 1.06 | 0.70 | 0.94 |
| Urinary L-PGDS index (mg/g creatinine) | 13.66* | 12.21* | 5.79 | 14.94* | 7.05* | 9.80* |
| [2 years later] | | | | | | |
| Blood creatinine concentration (mg/dl) | 1.3* | 5.5* | 3.4* | 0.6 | 1.1* | 0.7 |
| Urinary albumin index (mg/g creatinine) | 64.9* | 373.8* | 269.0* | 29.1 | 103.2* | 8.8 |
| Blood L-PGDS concentration (μg/ml) | 2.03* | 6.91* | 1.73* | 1.14 | 1.37* | 1.12 |
| Urinary L-PGDS index (mg/g creatinine) | 14.60* | 17.57* | 19.59* | 5.10 | 7.75* | 6.72* |

*Abnormal values

As shown in Table 1, all of the 6 patients were normal in both serum creatinine concentration and urinary albumin index at the beginning of the test. Two years later, however, 4 patients out of the 6 exhibited abnormal values in both serum creatinine concentration and urinary albumin index, urinary L-PGDS index) or more was considered abnormal. As to serum creatinine concentration, 1.1 mg/dl or more was considered abnormal. As to urinary albumin index, 30 mg/g creatinine or more was considered abnormal. The results are shown in Table 2.

TABLE 2

Follow-up Survey on Outpatients with Internal Diseases

|  | Subject 1 | Subject 2 | Subject 3 | Subject 4 | Subject 5 | Subject 6 | Subject 7 | Subject 8 |
|---|---|---|---|---|---|---|---|---|
| [At the beginning of the test] | | | | | | | | |
| Blood creatinine concentration (mg/dl) | 0.7 | 0.9 | 1.0 | 0.7 | 0.7 | 0.8 | 0.6 | 0.6 |
| Urinary albumin index (mg/g creatinine) | 9.5 | 10.0 | 22.1 | 12.3 | 5.8 | 20.5 | 15.9 | 8.8 |
| Blood L-PGDS concentration (μg/ml) | 2.03* | 1.68* | 1.88* | 1.39* | 0.89 | 0.79 | 1.20 | 1.03 |
| Urinary L-PGDS index (mg/g creatinine) | 16.51* | 8.87* | 15.55* | 5.44 | 6.74* | 11.94* | 14.58* | 7.62* |
| [2 years later] | | | | | | | | |
| Blood creatinine concentration (mg/dl) | 1.2* | 0.8 | 3.2* | 2.7* | 1.2* | 1.3* | 0.9 | 0.7 |
| Urinary albumin index (mg/g creatinine) | 47.2* | 9.5 | 523.3* | 633.7* | 349.0* | 98.5* | 14.0 | 7.0 |
| Blood L-PGDS concentration (μg/ml) | 1.38* | 1.16 | 2.08* | 3.21* | 1.61* | 1.23* | 1.07 | 0.93 |
| Urinary L-PGDS index (mg/g creatinine) | 7.93* | 9.27* | 16.52* | 22.74* | 9.60* | 17.77* | 13.41* | 5.72 |

*Abnormal values showing clearly that they developed nephropathy. This indicates that extremely early-stage renal disease(s) which is undetectable by current clinical diagnosis can be detected by determining L-PGDS concentrations. As to determined concentrations, it has become clear that it is appropriate to judge those subjects positive who show the mean value+(2× standard deviation) obtained from healthy subjects or greater than this value.

EXAMPLE 5

Prospective Study of Internal Medicine Outpatients

A two-year prospective study was performed on the 8 patients who were normal in both serum creatinine concentration and urinary albumin index but abnormal in serum L-PGDS concentration and/or urinary L-PGDS index in Example 1. In this study, abnormal values were defined as follows. As to L-PGDS, the mean value +(2×standard deviation) obtained from healthy subjects (i.e., 1.22 μg/ml for serum L-PGDS concentration and 6.16 mg/g creatinine for As shown in Table 2, all of the 8 patients were normal in both serum creatinine concentration and urinary albumin index at the beginning of the study. Two years later, however, 5 patients out of the 8 exhibited abnormal values in both serum creatinine concentration and urinary albumin index, showing clearly that they developed a renal disease(s). This indicates that extremely early-stage nephropathy which is undetectable by current clinical diagnosis can be detected by determining L-PGDS concentrations. As to determined concentrations, it has become clear that it is appropriate to judge those subjects positive who show the mean value+(2×standard deviation) obtained from healthy subjects or greater than this value.

EXAMPLE 6

Disease State Management for Glomerular Lesions

Creatinine clearance (24 hr), serum L-PGDS concentration and urinary L-PGDS index were determined on patients with glomerulonephritis and patients with chronic renal failure (total 11 patients). For the determination of urinary L-PGDS index, spotted urine samples were used. The results are shown in FIG. 6.

Figure 6:
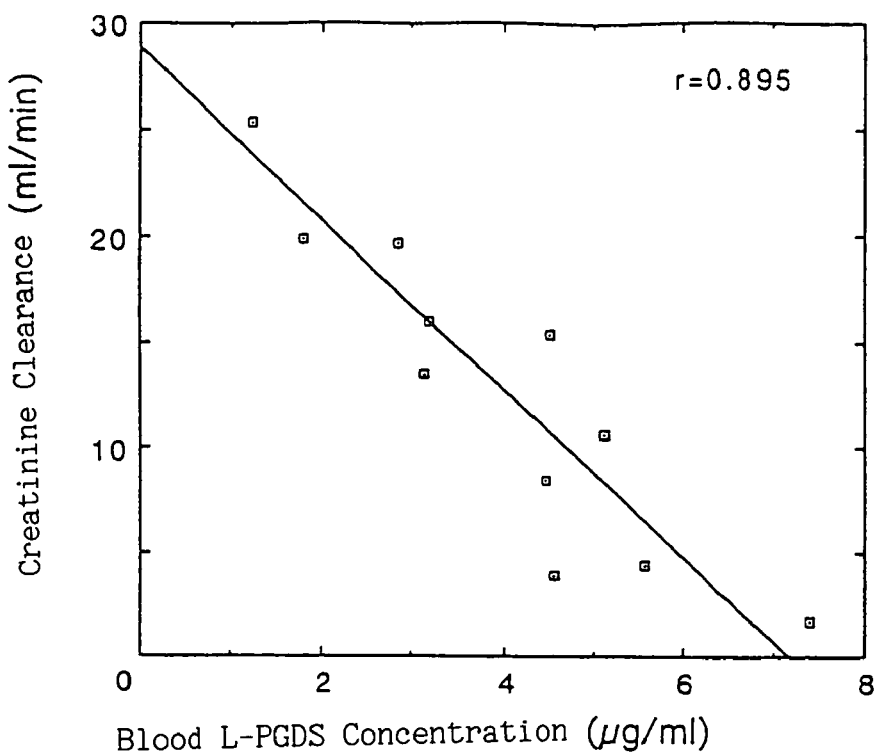
FIG. 6 shows correlation between serum L-PGDS concentration and creatinine clearance (Panel A) and correlation between urinary L-PGDS index and creatinine clearance (Panel B).
Figure 6:
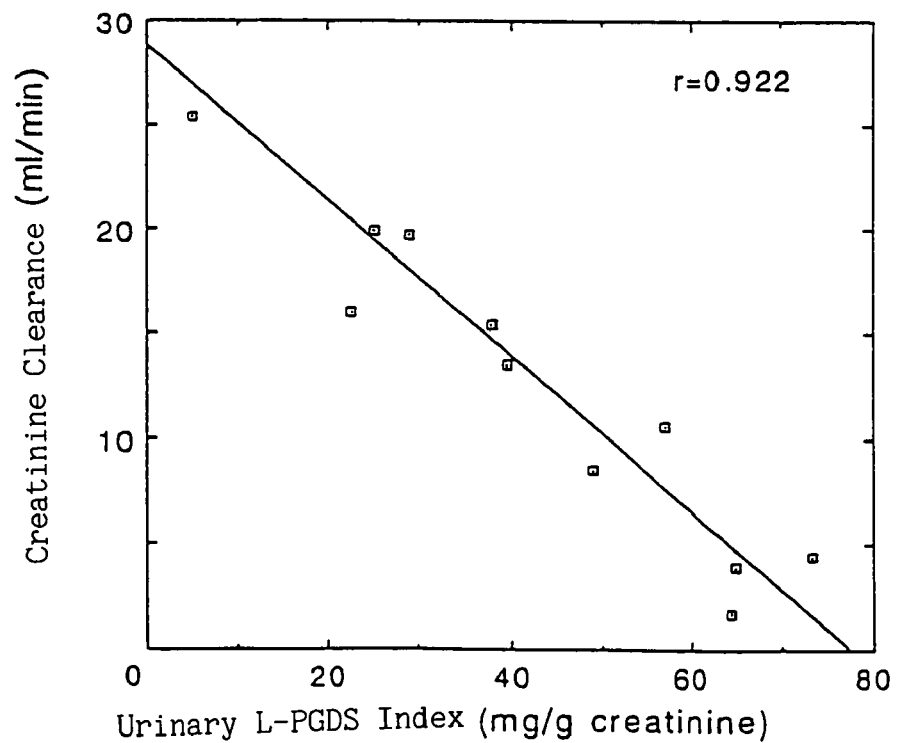

As shown in FIG. 6, both serum L-PGDS concentration and urinary L-PGDS index exhibited a high correlation with creatinine clearance. Thus, it has become clear that the determination of L-PGDS concentration is useful for the evaluation of glomerular filtration ability. Since the determination of L-PGDS concentration does not require timed urine nor administration of an exogenous substance to be cleared, this method has made it possible to manage the disease state of glomerular lesions simply.

EXAMPLE 7

Progress of Diabetic Nephropathy and L-PGDS Concentration

Urinary L-PGDS index was determined on 101 diabetic patients. At the same time, urinary albumin index and urinary type-IV collagen index were also determined. The degrees of progress of diabetic nephropathy were classified into normoalbuminuria stage (urinary albumin index<30 mg/g creatinine; 57 patients), microalbuminuria stage (30 mg/g creatinine ≦urinary albumin index<300 mg/g creatinine; 27 patients) and overproteinuria stage (urinary albumin index≧300 mg/g creatinine; 17 patients). The results are shown in FIG. 7.

Figure 7:
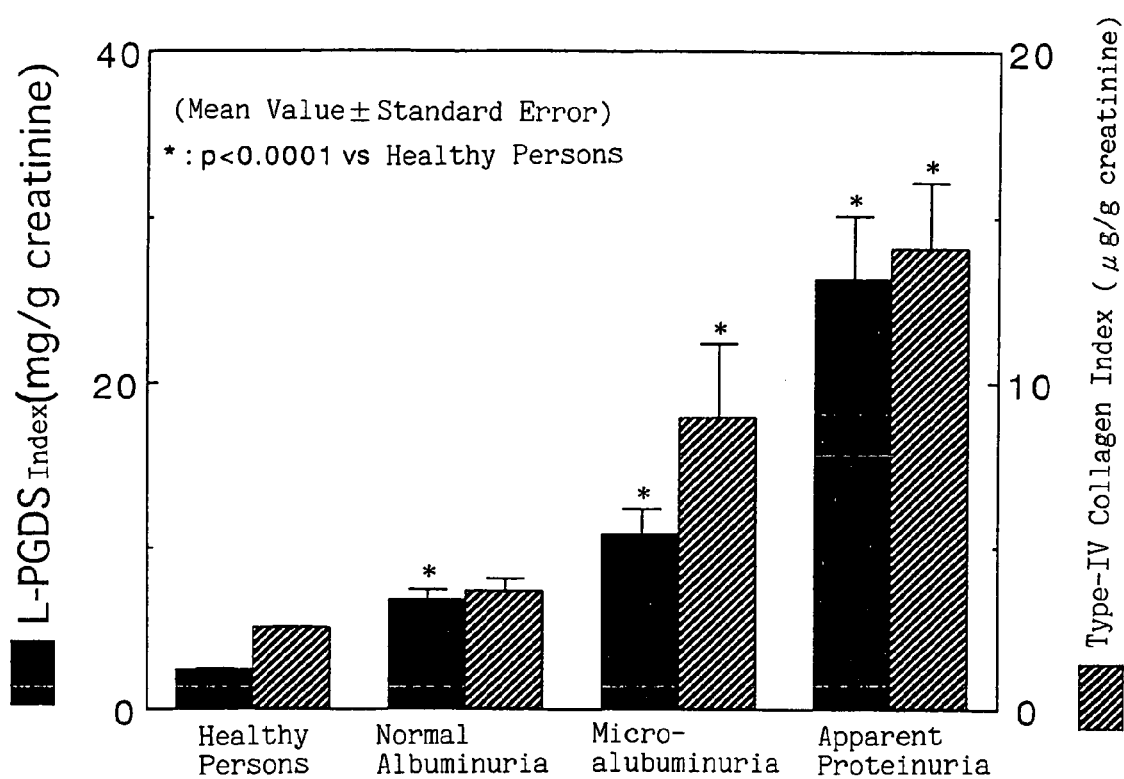
FIG. 7 shows changes in urinary L-PGDS index and urinary type-IV collagen index at various albuminuria stages classified based on urinary albumin index.

As shown in FIG. 7, it has become clear that both urinary L-PGDS index and urinary type-IV collagen index increase as diabetic nephropathy progresses. Therefore, we can say that urinary L-PGDS can be an indicator of early-stage diabetic renal diseases which is comparable to urinary albumin or urinary type-IV collagen.

Further, it was found that although the urinary L-PGDS indexes of diabetic patients at normoalbuminuria stage were significantly higher than those of healthy subjects, such significant difference is not recognized in urinary type-IV collagen indexes. This indicates that extremely early-stage diabetic nephropathy which is undetectable by determining urinary albumin or urinary type-IV collagen can be detected by determining urinary L-PGDS.

EXAMPLE 8

Progress of Diabetic Nephropathy and Positive Ratios

Positive ratios based on urinary L-PGDS index and urinary type-IV collagen index were examined in those patients at various albuminuria stages described in Example 7. In this examination, abnormal values were defined as follows. As to urinary L-PGDS index, 6.16 mg/g creatinine or more was considered abnormal according to Example 5. As to urinary type-IV collagen index, 3.7 µg/g creatinine or more was considered abnormal according to the standard set by Isono et al. (Motohide Isono et al., J. Jpn. Diab. Soc., 39, 599–604, 1996). For each index, patients showing an abnormal value were judged positive. The results are shown in FIG. 8.

Figure 8:
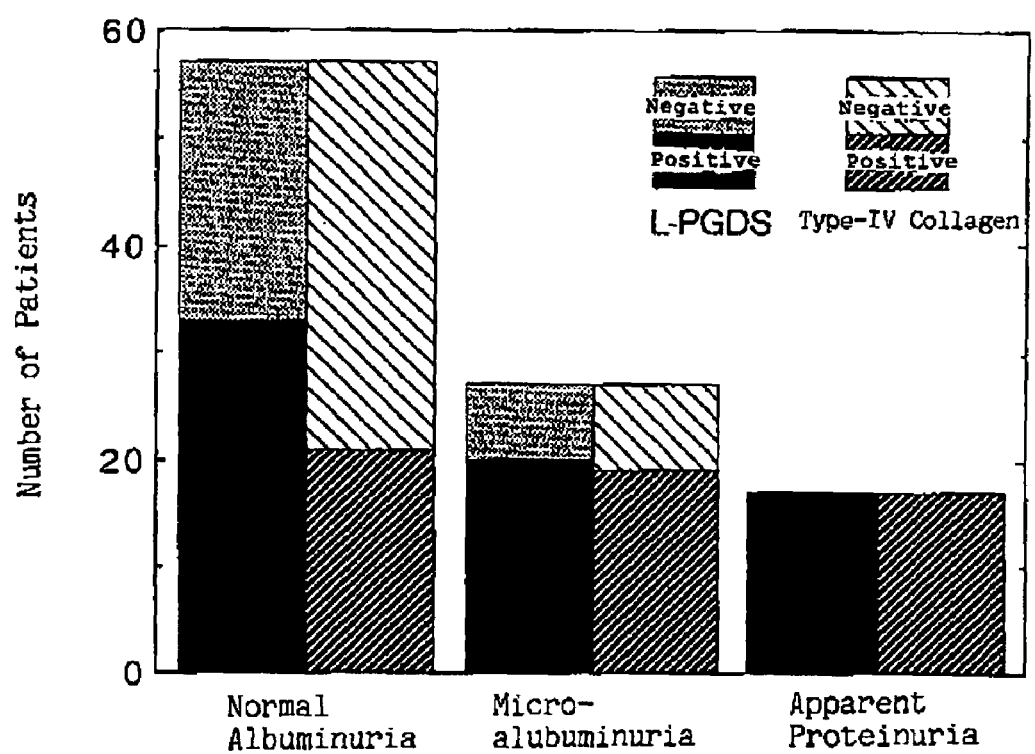
FIG. 8 shows positive ratios judged by urinary L-PGDS index and urinary type-IV collagen index at various albuminuria stages classified based on urinary albumin index.

As shown in FIG. 8, the patients at overproteinuria stage were 100% positive based on both urinary L-PGDS index and urinary type-IV collagen index. However, in the patients at microalbuminuria stage, the positive ratio based on urinary L-PGDS index was slightly higher than the positive ratio based on urinary type-IV collagen index (74.1% vs. 70.4%). In the patients at normoalbuminuria stage, the positive ratio based on urinary L-PGDS index was greatly higher than the positive ratio based on urinary type-IV collagen index (57.9% vs. 36.8%).

Further, these 101 diabetic patients were classified into two groups (i.e. positive group and negative group) with the reference value for urinary type-IV collagen index, and then positive ratio based on urinary L-PGDS index was examined in each group. The results are shown in FIG. 9.

Figure 9:
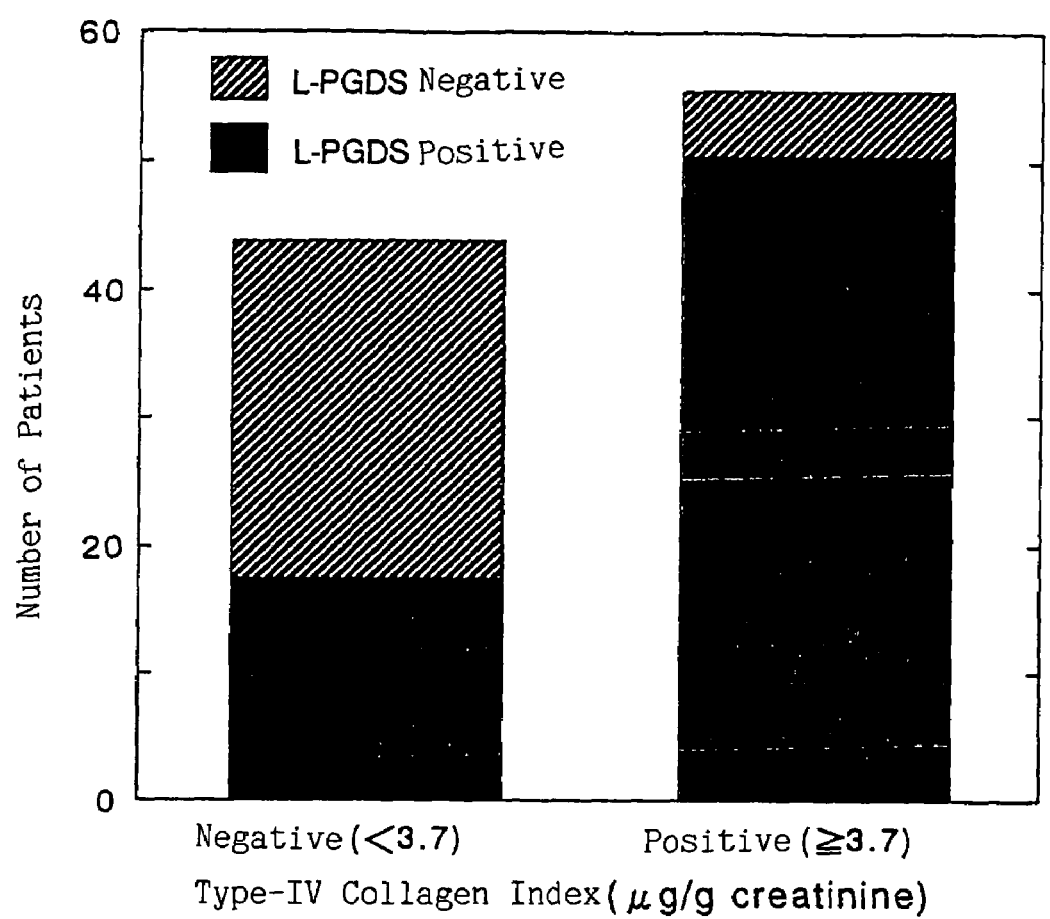
FIG. 9 shows positive ratios judged by urinary L-PGDS index in a group of diabetic patients positive in type-IV collagen index and a group of diabetic patients negative in this index.

As shown in FIG. 9, in the urinary type-IV collagen index positive cases, more than 90% were also judged positive in urinary L-PGDS index. Thus, the results from both indexes were almost consistent with each other. On the other hand, 40% of the urinary type-IV collagen index negative cases were judged positive in urinary L-PGDS index.

These results indicate that extremely early-stage diabetic nephropathy which is undetectable by determining urinary albumin or urinary type-IV collagen can be detected by determining urinary L-PGDS.

EXAMPLE 9

Retrospective Study of Diabetic Patients

L-PGDS index, albumin index and type-IV collagen index were determined on those 63 patients from the subjects in Example 7 whose urine samples had been taken 2 to 3 years prior to the present test and stored at −20° C. In this study, abnormal values were defined as follows. As to urinary albumin index, 30 mg/g creatinine or more was considered abnormal according to the diagnostic standard set by the joint committee of the Japan Diabetes Society and the Japanese Society of Nephrology. As to urinary L-PGDS and type-IV collagen indexes, abnormal values were defined in the same manner as in Example 8.

The results have revealed that there are 8 patients who are normal in both urinary albumin index and urinary type-IV collagen index in stored urine samples but judged positive in urinary L-PGDS index alone. For these 8 patients, past (2 to 3 years ago) and present urinary L-PGDS indexes, albumin indexes and type-IV collagen indexes are summarized in Table 3.

TABLE 3

Retrospective Survey on Diabetic Patients

|  | Subject 1 | Subject 2 | Subject 3 | Subject 4 | Subject 5 | Subject 6 | Subject 7 | Subject 8 |
|---|---|---|---|---|---|---|---|---|
| [In the past] | | | | | | | | |
| Albumin index (mg/g creatinine) | 9.6 | 10.9 | 2.3 | 18.9 | 6.7 | 0.6 | 8.8 | 5.7 |
| Type-IV collagen index (µg/g creatinine) | 2.6 | 1.5 | 1.2 | 2.2 | 1.1 | 2.7 | 3.0 | 3.5 |
| L-PGDS index (mg/g creatinine) | 6.60* | 9.68* | 10.34* | 9.08* | 6.43* | 7.89* | 7.09* | 6.79* |
| [At present] | | | | | | | | |
| Albumin index (mg/g creatinine) | 55.3* | 234.4* | 51.1* | 12.3 | 39.5* | 31.0* | 9.9 | 31.8* |
| Type-IV collagen index (µg/g creatinine) | 9.1* | 22.8* | 7.3* | 11.6* | 2.6 | 10.0* | 3.7* | 3.8* |
| L-PGDS index (mg/g creatinine) | 9.41* | 16.12* | 13.44* | 8.12* | 6.28* | 16.29* | 4.93 | 10.21* |

*Abnormal values

As seen from past and present urinary L-PGDS index data, only one patient (Subject 7) has achieved a normal value and the remaining seven patients still show an abnormal value in this index. Of these seven patients, one (Subject 5) has begun to show an abnormal value in urinary albumin index also and two (Subjects 4 and 7) have begun to show an abnormal value in urinary type-IV collagen index also in two to three years. In addition, five patients (Subjects 1, 2, 3, 6 and 8) have begun to show an abnormal value in both urinary albumin index and urinary type-IV collagen index.

These results indicate that extremely early-stage diabetic nephropathy which is undetectable by determining urinary albumin or urinary type-IV collagen can be detected by determining urinary L-PGDS.

INDUSTRIAL APPLICABILITY

According to the present invention, there is provided a method which can detect renal abnormalities more remarkably than serum creatinine and urinary albumin which are used as an indicator of renal diseases accompanied with glomerular lesions, such as glomerulonephritis and diabetic nephropathy. Furthermore, the method of the invention can detect, with extreme accuracy and less burden to subjects, even those renal diseases prior to early nephropathy stage which exhibit no abnormality in serum creatinine, urinary albumin and urinary type-IV collagen and are undetectable by current clinical diagnosis. Additionally, according to the method of the invention, glomerular filtration ability can be evaluated simply without timed urine or administration of an exogenous substance to be cleared. Thus, the method of the invention is extremely useful for detection of early-stage renal diseases and disease state management for patients with such diseases.

The invention claimed is:

1. A method of detection of an early-stage renal disease, the method comprising:
   determining the concentration of albumin in a urine sample of a test subject to be normal, the first determination failing to detect early-stage renal disease in the subject; and
   determining a concentration of human lipocalin-type prostaglandin D synthase (L-PGDS) then in a urine sample taken from the same test subject,
   wherein a higher concentration of human L-PGDS in the urine sample taken from the test subject, compared to a reference value of human L-PGDS concentration in urine, is an indication that the test subject has early-stage renal disease, wherein the reference value is obtained by determining the concentration of human L-PGDS in urine of healthy subjects.

2. The method of claim 1, wherein the determination of the concentration of human L-PGDS in a urine sample from the test subject is performed by an immunological assay.

* * * * *